United States Patent [19]
Hunt et al.

[11] Patent Number: 6,018,106
[45] Date of Patent: Jan. 25, 2000

[54] USE OF YEAST POLY (A) BINDING PROTEINS AND THEIR GENES FOR BROAD RANGE PROTECTION OF PLANTS AGAINST BACTERIAL, FUNGAL AND VIRAL PATHOGENS

[75] Inventors: Arthur G. Hunt; Qing-Shun Li, both of Lexington, Ky.; Jianjun Yang, Ithaca, N.Y.; Carol Von Lanken, Lexington, Ky.

[73] Assignee: University of Kentucky Research Foundation, Lexington, Ky.

[21] Appl. No.: 09/116,879

[22] Filed: Jul. 16, 1998

[51] Int. Cl.[7] .............................. A01H 5/00; C12N 5/14; C12N 15/82
[52] U.S. Cl. ..................... 800/301; 435/419; 800/279; 800/288; 800/294; 800/298
[58] Field of Search ............... 435/69.1, 320.1, 435/419, 468, 469; 536/23.74; 800/279, 288, 294, 301, 298, 320, 320.1, 320.2, 320.3, 317.2, 317.3, 317.4, 313, 307, 309, 314, 315

[56] References Cited

PUBLICATIONS

Adam SA, et al. "mRNA polydenylate–binding protein: Gene isolation and sequencing and identification of a ribonucleoprotein consensus sequence." Mol. Cell. Biol. 6: 2932–2943, Aug. 1986.
Sachs AB, "A single gene from yeast for both nuclear and cytoplasmic polyadenylate–binding proteins: Domain structure and expression." Cell 45: 827–835, Jun. 1986.
Le, Hanh et al. "The Wheat Poly (A)–Binding Protein Functionally Complements pab 1 in Yeast, " *Eur. J. Biochem.*, vol. 243, pp. 350–357 (1997).
Belostotsky, Dmitry A. et al. "Differential Organ–Specific Expression of Three Poly (A)–Binding–Protein Genes from *Arabidopsis thaliana*," *Proc. Natl. Acad. Sci. USA*, vol. 90, p. 6686–6690 (Jul. 1993).
Berger, Lloyd C. et al. "Translation of Poly (A)–Binding Protein mRNA is Regulated by Growth Conditions," *Biochem. Cell Biol.*, vol. 70, pp. 770–778 (1992).
Anderson, James T. et al. "PUB1 is a Major Nuclear and Cytoplasmic Polyadenylated RNA–Binding Protein in *Saccharomyces cerevisiae*," *Mol. Cell. Biol.*, vol. 13, No. 10, pp. 6102–6113 (Oct. 1993).

*Primary Examiner*—Lynette R. F. Smith
*Assistant Examiner*—Amy J. Nelson
*Attorney, Agent, or Firm*—McDermott, Will & Emery

[57] ABSTRACT

Plants that accumulate the yeast polyadenylate binding protein (yPAB) display a range of abnormalities, including a characteristic chlorosis in leaves to a necrosis and pronounced inhibition of growth. The severity of these abnormalities reflects the levels of yeast PAB expression in the transgenic plants. In contrast, no obvious differences are seen in undifferentiated callus cultures that express the same range of yeast PAB. The expression of the yeast PAB1 gene in plants does not affect expression of the plant PAB gene family or alter poly(A) length in the total RNA population. It is proposed that the yeast PAB1 gene or its product interferes with as yet unidentified functions of PABs, which functions are manifest only in differentiated, developed plants. Surprisingly, transgenic plants expressing the yeast PAB1 gene are also observed to have a systemic acquired resistance (SAR) to bacterial, fungal and viral pathogens.

20 Claims, 5 Drawing Sheets

USE OF YEAST POLY (A) BINDING PROTEINS AND THEIR GENES FOR BROAD RANGE PROTECTION OF PLANTS AGAINST BACTERIAL, FUNGAL AND VIRAL PATHOGENS

STATEMENT OF GOVERNMENT SUPPORT

The present invention was developed in part with support received from a U.S. Department of Agriculture—University of Kentucky Cooperative Agreement (#58-43YK-7-0025) and USDA Grant #89-37262-4835. The Government may have certain rights in the invention.

TECHNICAL FIELD

The present invention is related to the field of transgenic plants. Among the observed phenotypes of the transgenic plants is a systemic acquired resistance (SAR) to bacterial, fungal and viral pathogens.

BACKGROUND OF THE INVENTION

Polyadenylate binding proteins (PABs) play important roles in gene expression. In yeast, they are involved in recruitment of large ribosomal subunits to form the translation initiation complex (1), and for the progressive shortening of polyadenylate tracts on cytoplasmic mRNAs (1). PABs also play important roles in gene expression in plants. In particular, they presumably mediate the poly(A)-cap synergism that is required for optimal translation of mRNAs in plant cells (2).

PABs are highly conserved RNA-binding proteins that specifically bind the 3' polyadenylate tracts of cytoplasmic mRNAs. PABs from different organisms have a common region in the N-terminal two-thirds of the protein that consists of four repeating RNA-binding domains of 80 to 90 amino acid residues (3). Each domain contains two conserved motifs (the so-called RNP-1 and RNP-2 motifs; 4,5). There is also a conserved domain in the C-terminal regions of PABs (6), a domain separated from the RNA binding domains by a variable spacer region. It has been suggested that the N-terminal region determines poly(A)-binding activity and the C-terminal region mediates interactions between PABs and other proteins (3,6,7).

To date, most work with plant PABs has focused on the characterizations of purified proteins and clones for PABs. Sieliwanowicz (8) described a protein in pea extracts that bound poly(A)-Sepharose and was able to stimulate translation in a cell-free system. Yang and Hunt (9) previously described the purification and characterization of a 70 kD PAB from the leaves of young pea seedlings. This protein was similar to pea PAB described by Sieliwanowicz (8) and had RNA binding properties similar to those of PABs from other organisms. Three Arabidopsis PAB genes have been isolated and characterized (6,10). One Arabidopsis gene codes for a protein with extensive similarity to PABs from other organisms but is novel in that it is expressed only in flowers (10). Another Arabidopsis PAB gene is expressed in root and shoot tissues (6), suggesting that different forms of PAB may exist in different tissues in plants. Gallie (2) inferred a positive role for plant PABs in translation, based on the increased translatability of polyadenylated RNAs in isolated tobacco protoplasts. These studies also suggested a link between the presence of a 5' cap and a 3' polyadenylate tract in an RNA, as a 5' cap was needed for the enhanced translatability provided by a 3' polyadenylate tract. This feature was not unique to plant cells, as it was also observed in Chinese hamster ovary and yeast cells (2).

As described herein, a yeast PAB gene is expressed in a plant, e.g., the yeast PAB1 gene in tobacco. The utility of this gene as a potential trans-dominant marker to probe PAB function in plants can then be assessed. A cDNA encoding a wheat PAB protein has been transformed in yeast, where it was observed to functionally complement a PAB1 mutant yeast, suggesting that this monocot protein can function in yeast (25). Apparently, however, the reverse approach, transforming a differentiated higher plant with a yeast PAB gene, has not previously been explored.

SUMMARY OF THE INVENTION

It has now been observed that transformed plants, which express the yeast PAB1 gene, are impaired in growth and development. The severity of the observed impairment corresponds to the quantity of yeast PAB (yPAB) seen in the transgenic plants, and is not caused by a cosuppression of expression of the endogenous tobacco PAB genes. Interestingly, the growth impairment is seen in regenerated plants, but not in plant cell cultures. At a minimum, these observations suggest that the yeast PAB1 gene should be a useful tool for the further characterization of plant mRNA translation and metabolism.

It is also observed that the resistance of a plant to a bacterial, fungal or viral pathogen is enhanced when the plant is transformed with a yeast PAB1 gene or its encoded product. Thus, a method of enhancing the pathogen resistance of a plant comprises transforming it with a polynucleotide that encodes a yPAB protein, and maintaining the transformed plant under conditions effective to express the yPAB protein. In a preferred embodiment, an aforementioned polynucleotide encodes the yeast PAB1 protein.

Although the precise mode(s) by which a yPAB gene or protein is effective in enhancing pathogen resistance is presently unclear, it is believed that the RNA-binding ability of the PAB1 protein plays a central role in imparting such resistance perhaps by interfering with one or more "normal" cellular processes, which trigger local defense responses and eventually systemic acquired resistance (SAR). Thus, it is likely that plants transformed with a yPAB coding sequence according to the present invention can be protected from infections by a wide range of normally compatible bacterial, fungal and viral pathogens.

A preferred aspect of the present invention entails providing a self-regulatory function to expression of the yPAB protein in the transgenic plant so that pathogen resistance is achieved without adversely affecting growth of the plant. One means of achieving such self-regulation is by linking a lac repressor gene to a pathogen resistance (PR) promoter in a suitable vector, e.g., a pKYLX7 vector. Transgenic plants carrying such an assembly of regulatory elements can express the yPAB protein to levels that trigger defense responses, which in turn cause lac repressor to accumulate and suppress further expression of yPAB protein. A "constitutive" SAR to pathogens is thereby induced without substantially compromising the growth of new leaves.

DETAILED DESCRIPTION OF THE INVENTION

Figure 1:
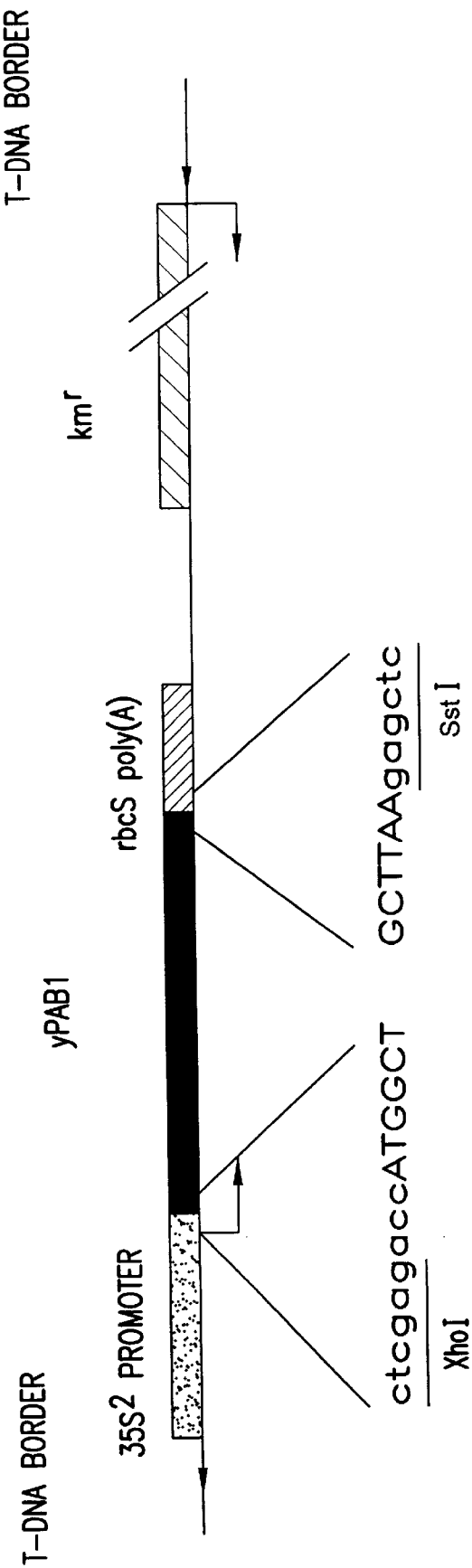
FIG. 1 shows the structure of the chimeric gene containing the yeast PAB1 gene and its position in the micro-T-DNA present in pKYLX71:35S$^2$. The promoter present in this plasmid is a modified cauliflower mosaic virus 35S promoter that contains a duplication of the enhancer region; it has been described in detail elsewhere (13).

The present invention concerns a method of providing or enhancing resistance of a plant to a bacterial, fungal or viral pathogen. The method comprises transforming the plant with a polynucleotide encoding a yeast polyadenylate binding protein (yPAB), and maintaining the plant under conditions effective to express the yPAB.

The plant is transformed using a method suited for the particular species. Many different protocols are available, for instance, by transforming callus cultures or leaf explants. Preferably, the transformation is performed using an Agrobacterium vector that encodes the yPAB.

In a preferred embodiment, a polynucleotide encoding a yPAB is one that encodes a yeast PAB1 protein. Accordingly, the polynucleotide preferably includes a coding sequence of the yeast PAB1 gene. The coding sequence can be obtained by direct synthetic techniques, restriction excision of genomic material, excision of extrachromosomal DNA material containing the gene, or by generation of cDNA from mRNA encoding the yPAB1 protein. Conventional genetic engineering techniques such as those set forth in Sambrook J. et al., *Molecular Cloning*, $2^{nd}$ ed., can be employed.

An expression vector in which the polynucleotide encoding a yPAB protein is provided is additionally provided with the regulatory domains necessary to effect transcription of the yPAB-encoding polynucleotide. One feature of such a regulatory domain is the promoter sequence, which is typically provided upstream of the yPAB-encoding sequence and is operably linked thereto. A CaMV promoter, such as the $35S^2$ promoter containing a double enhancer region, is preferred. The expression vector can be in the form of a linear or circularized plasmid or as a virus, which contains the nucleic acids either as DNA or complementary RNA.

In order to avoid deleterious over-expression of the yPAB protein, which can cause excessive stunting of growth, it is desired to "feedback" the level of expression to the regulatory elements controlling transcription. For instance, a yeast PAB1 encoding sequence can be operably linked to a CaMV 35S promoter into which one or more lac operator sequences have been inserted. The positions of these sequences can be optimized for repression of yPAB1 expression in the presence of the lac repressor. In addition, the lac repressor (lacI) gene can be linked to a PR (pathogen resistance) gene promoter using standard techniques and cloning strategies. Plants transformed with these elements, e.g., as part of an expression vector, can express the PAB1 protein, thereby inducing a defense response. Expression of the lacI gene can, in turn, be induced since it is under the control of the PR promoter. Once lac repressor accumulates, further expression of the PAB1 gene can be suppressed, thereby eliminating the harmful effects of expression of these genes. Initial or exploratory studies can be performed on tobacco using pKYLX7 as a "base vector." Protocols and vectors employing the lac operator/promoter are described herein and by Sambrook et al. The PR promoter and its use in a cloning vehicle are described herein and previously (24).

A plant host targeted with an expression vector of the present invention is one effectively transformed with a yPAB-encoding polynucleotide. The plant host is typically a monocot or dicot, and includes corn, rice, wheat, maize, alfalfa, oats, barley, rye, sorghum, clover, tobacco, tomato, pea, potato, cauliflower, beans, cucumber, beet, turnip, spinach, kale, cabbage, squash, melon, cotton, apple, peach, plum, among others. Of course, the plant need not be in its adult differentiated state. Seeds, gern lines, leaf explants, and callus cultures transformed with nucleic acids encoding a yeast PAB protein are also contemplated. The induced SAR can cause the plant to show resistance to subsequent infection by a wide range of normally compatible pathogens (27).

Representative plant bacterial pathogens, for which a transformed plant can be provided with enhanced resistance, are listed in Table 1 by genus and associated disease.

Representative groups of fungal pathogens of plants, to which a plant transformed according to the principles of the present invention can be provided with enhanced resistance, include Ascomycetes, Basidiomycetes, Zygomycetes, Oomycetes, Deuteromycetes, Peronosporomycetes, Chytridiomycota, Zygomycota, Plectomycetes, Loculoascomycetes, Discomycetes, Pyrenomycetes, Heterobasidiomycetes, Homobasidiomycetes, Teliomycetes, Ustomycetes, Septomycetes, Saprolegniomycetidae, and Plasmodiophorida, and the like.

Representative plant viruses that a transformed host can show enhanced resistance against include those listed in Table 2. Particularly preferred, at least for further exploratory studies, is tobacco mosaic virus (TMV). Cytoplasmic plant viruses, i.e., those for which the viral nucleic acids remain extrachromosomal following infection, are expected to be especially susceptible to inhibition with a yPAB due to their presence in the cytosol.

Whenever the plant is transformed as described herein and the transformation is stably maintained by the organism, the pathogen resistance trait of the yPAB is inheritable. Coincident with acquiring the pathogen resistance is activation of a pathogen resistance (PR) gene of the plant. As noted above, this aspect of pathogen response can be employed to provide a self-regulatory function to expression of a yPAB protein. In particular, plants can be obtained that have one older leaf (or sector thereof) that contains detectable expression of yPAB protein, while younger leaves contain no yPAB protein due to suppression of transcription of the nucleotide sequence encoding this protein. However, the younger leaves are resistant to a broad range of pathogens due to induction of the "constitutive" SAR upon expression of yPAB in the older leaf.

A related aspect of the present invention is a plant transformed with a polynucleotide encoding a yeast PAB protein. Thus, the plant preferably is transformed with a polynucleotide that includes a yPAB encoding sequence. As demonstrated herein, a yeast PAB1 encoding sequence can be operably linked to a $35S^2$ promoter for efficient transcription. A plant so transformed has an enhanced resistance to a bacterial, fungal or viral pathogen relative to the resistance of a plant not transformed with such a polynucleotide. A preferred expression vector is Agrobacterium containing an insert of the aforementioned polynucleotide.

For purposes of clarity and understanding, the invention will now be illustrated by certain examples, but is not limited by these examples.

EXAMPLES

Example 1

Recombinant DNA Manipulations

Recombinant DNA manipulations, PCR reactions, and DNA sequencing were carried out using standard protocols (15,16). To clone the yeast PAB1 gene for expression in plants, the following oligonucleotide primers were used:

5' . . . TTCTCGAGACCATGGCTGA-TATTACTGATAAG . . . 3' (SEQ ID NO: 1)

5' . . . TTGAGCTCTTAAGCTTGCTCAGTTTGT-TG . . . 3' (SEQ ID NO: 2).

The yeast PAB1 gene was amplified by PCR using 35 cycles consisting of 1 min at 92° C., 1 min at 55° C., and 2 min at 72° C. The resulting oligos were subcloned into pBluescript (Stratagene, La Jolla, Calif.) to confirm their sequence and then the PAB1 gene was cloned as an NcoI-SstI fragment into the plant expression vector pKYLX71-$35S^2$ (11).

Example 2

Plant Transformations and Callus Cultures

Recombinant expression plasmids were transferred into *Agrobacterium tumefaciens* C58C1::pGV3850 (17) by triparental mating (18) and transconjugant Agrobacteria used to transform tobacco. For this, sterile leaf disks (12) were incubated with Agrobacterium suspensions (in Luria broth [15]; ca. $10^9$ cells/mL) for 5–15 min, then transferred to MS agar media (19) containing 3% sucrose, 2.5 mg/L benzylaminopurine (BA), and 1 mg/L indole-3-acetic acid (IAA). After 2–3 days on this media, leaf explants were transferred to the same media supplemented with 300 mg/L kanamycin and 500 mg/L Mefoxin (Merck, Sharpe, and Dohme, Rahway, N.J.); these explants, and the resulting callus cultures, were transferred to fresh media 1–2 times per week. Regenerating shoots were transferred to rooting media (MS agar containing 3% sucrose and 500 mg/L Mefoxin); rooted plants were then transferred to soil and maintained in the greenhouse. In some instances, callus cultures were maintained for several months on MS agar media containing 3% sucrose, 2.5 mg/L benzylaminopurine (BA), 1 mg/L indole-3-acetic acid (IAA), 300 mg/L kanamycin, and 500 mg/L Mefoxin.

Example 3

Protein Extraction

Denatured tissue extracts were prepared for immunoblot analysis to minimize protein degradation. For this purpose, 300 mg of leaf tissue was collected from comparably aged leaves of young plantlets (4–6 leaf stage); this was necessary to permit sampling of leaves that were laregly devoid of necrotic areas. Leaf tissue was homogenized in 200 μL of 2xSDS-PAGE sample buffer (0.125 M Tris HCl, pH 6.8, 20% [v/v] glycerol, 2% [w/v] SDS, 10% [v/v] b-mercaptoethanol, and 0.001% [w/v] bromphenol blue) and boiled for 10 min. After a brief centrifugation, cell debris was discarded and the supernatant was stored at −20° C.

To prepare non-denatured extracts for immunoprecipitations, between 1 and 2 g of leaf tissue from an appropriate plant was ground homogenized in 4 mL/g of Buffer A (100 mM KCl, 30 mM Tris-HCl, pH 8.0, 1 mM $CaCl_2$, 1 mM $MgCl_2$, 5 mM EDTA, 5 mM phenylmethyl-sulfonyl fluoride [PMSF], 15 mM β-mercaptoethanol, and 1.5 μg/mL each of leupeptin, chymostatin and antipain) using a mortar and pestle. Cell debris was removed by centrifugation and the supernatant stored at −20° C. The preparation was done at 0 to 4° C.

Example 4

Immunoblot Analysis

For immunoblots, the protein from 30 mg of leaf tissue was separated by SDS-PAGE and the separated proteins transferred to a nitrocellulose membrane (20) using a Trans-Blot Cell (Bio-Rad Laboratories, Richmond, Calif.) following the manufacturer's recommendations. Filters were probed with monoclonal antibodies specific for the yeast PAB (provided by Dr. Maurice Swanson, University of Florida) or polyclonal antibodies raised against the purified pea PAB (21). Briefly, filters containing transferred proteins were incubated (at room temperature) in TTBS (20 mM Tris-HCl, pH 7.5, 0.5 M NaCl, 0.05% [v/v] Tween 20) for 5 min, TTBS containing 5% (w/v) nonfat dried milk for 1 hr, and then with 5% milk-TTBS containing a 1:1000 dilution of antibody for 12–16 hr. The monoclonal antibody was removed with three washes (5 min each) of TTBS, the filters incubated for 3 hr with 5% milk-TTBS containing goat anti-mouse IgG alkaline phosphatase conjugate (for blots probed with the anti-yeast PAB) or goat anti-rabbit IgG alkaline phosphatase conjugate (for blots probed with the anti-pea PAB; Sigma), and this antibody conjugate removed with three washes of TTBS. Filters were equilibrated in AP buffer (0.1 M Tris-HCl, pH 9.5, 0.1 M NaCl, 0.05 M $MgCl_2$) and developed in AP buffer+2 mg/mL nitroblue tetrazolium+1.2 mg/mL 5-bromo-4-chloro-3-indoyl phosphate; development was stopped by washing with deionized water.

Example 5

Immunoprecipitations

PABs were immunoprecipitated from non-denatured protein extracts (see above) as follows. 650 mg of protein (in volumes ranging from 0.24 to 0.50 mL) were incubated with 2.5 mL of antibody (estimated protein content of 0.4 mg/mL) and incubated on ice for 4 hr with shaking. 25 mL of Protein A-agarose (Sigma Chemical Co., St. Louis, Mo.)

was then added and the suspension incubated for 30 min on ice. The Protein A-agarose was then collected by centrifugation (30 sec. in a microcentrifuge), washed three times with 400 $\mu$L PAB Buffer A, resuspended in 100 $\mu$L of 2×SDS-PAGE sample buffer, and boiled for 10 min. 25 $\mu$L were analyzed by SDS-PAGE and staining with Coomassie Brilliant Blue (15). PAB contents on these gels were estimated by comparison with standards and with the IgG bands.

Example 6

Poly(A) Length Determinations

RNA was isolated from single primary transformants by homogenizing leaf tissue in a guanidinium thiocyanate buffer (22) and pelleting through a cesium chloride gradient (23). To determine poly(A) lengths, 50 mg of total RNA from each plant line was precipitated with ethanol, dried under vacuum, and dissolved in 10 mL of water. To this was added 4 mL of 5×yeast PAP reaction buffer (U.S. Biochemicals, Cleveland Ohio) and 5 mL of [a-$^{32}$P]3'-dATP (about 1 mCi/mL in 1×yeast PAP reaction buffer, 3000–5000 Ci/mmol). One mL (300 units) of yeast PAP (U.S. Biochemicals) was added and the labeling mixture incubated at 30° C. for 1 hr. This mixture was then placed at 70° C. for 5 min and placed on ice. 100 ng of RNAse A (Boehringer-Mannheim, Indianapolis, Ind.) was added and the mixtures incubated at 37° C. for 1 hr. The sample was then diluted with 100 mL of TE (10 mM Tris HCl, pH 8.0, 1 mM EDTA) and extracted once with phenol/chloroform/isoamyl alcohol (25:24:1), once with chloroform, precipitated, dried, and analyzed by electrophoresis on 6% sequencing gels. Labeled poly(A) tracts were visualized by autoradiography.

Example 7

Bacterial Resistance Test

The tobacco bacterial pathogen *Pseudomonos syringe* pv. *tabaci* wild fire 4 (WF4, kindly provided by Dr. Sheng-Yang He, Michigan State University) was cultured in LB media at 30° C. An overnight culture was pelleted by centrifugation and resuspended in water to an $OD_{600}$ of 1.0. 20,000 and 200,000 fold dilutions were prepared from this suspension and used as inocula. Water was used as control in all experiments. These various inocula were applied to the undersides of selected leaves of 7–8 week old plants using a 1 mL syringe; sufficient inoculum to form a 10 mm diameter circle at the site of inoculation was applied. After 5–6 days of growth (between 22° C. and 25° C., with a 12/12 light/dark cycle), the inoculated leaves were removed and photographed.

To study the growth of WF4, leaves of three plants (in identical positions, and lacking noticeable PABL1-related "symptoms") were inoculated with the 1/20,000 dilution as described in the preceding section. After inoculation of the WF4 on the tobacco leaf, the infiltrated area was marked for easier sampling. At different times over the course of 6 days, two leaf discs (6 mm diameter) were taken from each infiltrated area, washed with 70% ethanol for two minutes, and rinsed with water 3 times. Each leaf disc was then ground in 100 mL sterile water and spun briefly. The supernatant was then diluted and spread on LB agar plate for colony counting.

Example 8

TMV resistance test

Tobacco mosaic virus (TMV, kindly provided by Dr. Wu, Department of Plant Pathology, University of Kentucky) was inoculated to leaves of 7–8 week old plants (6 duplicates per line). For this, serial dilutions of a TMV stock were made (yielding final virus concentrations of 0.5, 0.1 and 0.02 mg/mL, respectively) and 10 mL of each was applied to a leaf surface that had been previously treated with carborundum. Mock inoculations were done with water instead of diluted virus. After 7 days, inoculated leaves were removed and photographed.

Example 9

Reduction of Fungal Spore Production by Transgenic Tobacco Cell Lines

The effects of transformation of tobacco plants on spore production by the blue mold fungus *Peronospora tabacina* Adam was studied. In these studies *P. tabacina* Adam (obtained in Kentucky in 1979 and designated isolate 79) was maintained by weekly transfers of sporangiospores on young cv. Ky 14 tobacco plants. Prior to inoculations, sporangiospores on sporulating leaves were washed off in distilled water, washed three times with distilled water, and collected on 3.0 $\mu$m membranes. Sporangiospores were then resuspended in distilled water and the concentration was adjusted to 20×10$^3$ spores per mL. Six-week old plants were inoculated by spraying a uniform fine mist of the spore suspension on the upper surfaces of leaves. The plants were then covered with wet brown plastic bags and kept in the dark for 16 h. Plants were then uncovered and placed in a growth chamber.

In order to assess resistance to *P. tabacina*, the mean number of sporangiospores produced per cm$^2$ leaf area was estimated seven days after inoculation. Sporulation was induced by detaching upper leaves from each plant, placing them in a large petri dish containing wet filter paper, and the dishes were sealed and allowed to incubate overnight in a growth chamber. One upper leaf from four individual plants per line was excised for a total of four replications per line. The following day, sporulating tissue samples (approximately 2–3 cm$^2$) were excised, measured, and placed in tubes containing 10 mL of distilled water. Tubes with tissue samples were gently vortexed to detach sporangiospores from sporangiophores. The concentration of sporangiospores in these suspensions was estimated using a hemacytometer and the total number of sporangiospores in the solution was calculated. The total number of sporangiospores was then divided by the measured leaf area to obtain the number of sporangiospores produced per cm$^2$ of leaf area.

Example 10

RNA Preparation and Northern Blot Analysis

Total RNA was isolated from the upper leaves (in case of A11 line, only leaves without lesion were taken) of 7 to 8 week old plants, using Promega (Madison, Wis.) RNAgents total RNA Isolation Kit™. Equal amounts total RNA (10 mg) were separated on a 1.2% agarose gel, transferred to Immobilon N (Millipore, Bedford, Mass.), and hybridized with $^{32}$P-labeled PR-1b (24) DNA probe, and washed using standard protocols (15). These blots were visualized by autoradiography.

RESULTS

Recombinant DNA Manipulations and Plant Transformations

The coding sequence for the yeast PAB1 gene was tailored for expression in plants using appropriately designed oligonucleotides and subcloned, as a PCR product, into pBluescript. A resulting recombinant was sequenced in its entirety to assure the absence of possible PCR-derived changes in the PAB1 sequence. The PAB1 gene was then cloned from this plasmid as an NcoI-SstI fragment into pKYLX71-35S$^2$, a plant expression vector designed for use with *Agrobacterium tumefaciens* in transforming plants (11). The resulting plasmid (pKYLX71-35S$^2$: yPAB1; see FIG. 1) was mobilized from *E. coli* into *Agrobacterium tumefaciens* and the trans-conjugant Agrobacterium used to transform tobacco (12). For comparative purposes, callus and plant lines were also generated using a transformation vector containing a cat gene in place of the PAB1 gene (13).

Initially, four plants, derived from two independent callus cultures, were regenerated. However, all four of these failed to thrive (see below) and eventually died. In light of this, 21 additional independent callus lines were produced, and several plants regenerated from each callus line. With the exception of plants from one callus line, all of these plants survived, were fertile, and yielded seed upon self-fertilization. Plants from the other callus line grew very slowly and died after about two months.

Additionally, selected PAB1 callus lines were maintained in culture for an extended period (9 months). These different cultures were indistinguishable in terms of callus morphology or vigor of growth.

Transgenic Plants that Express the Yeast PAB1 Gene are Impaired in Growth

Figure 2:
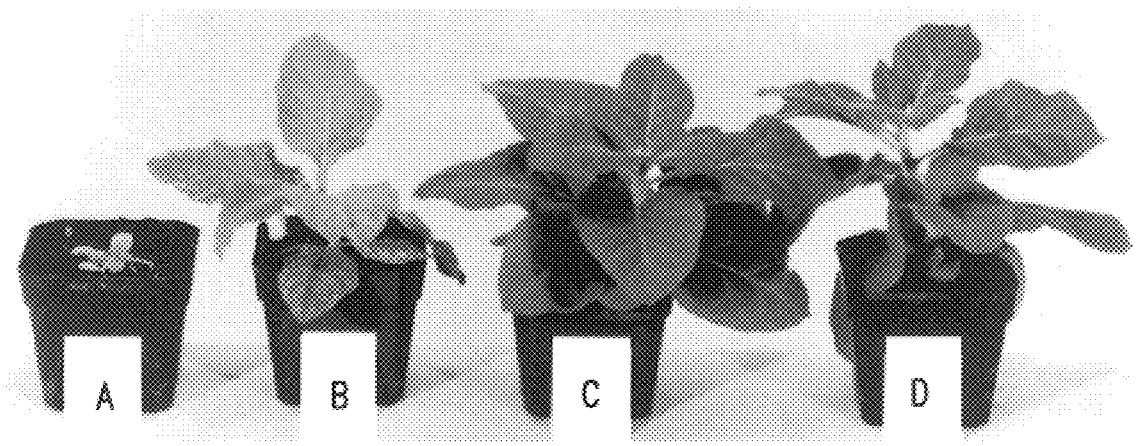
FIG. 2 depicts phenotypes of plants that express the yeast PAB1 gene. Primary transformants representative of plants regenerated from callus lines F6 (plant A), A11 (plant B), E2 (plant C), and a transformed control line (plant D) are shown.
Figure 3:
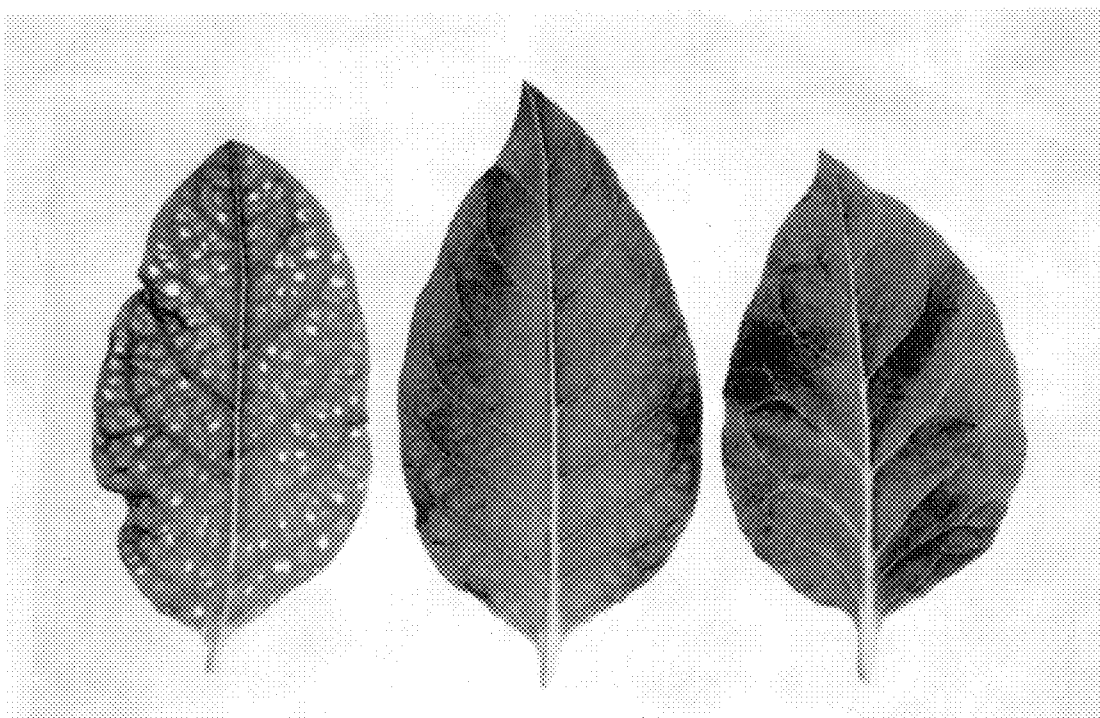
FIG. 3 illustrates the appearances of leaves from plants that express the yeast PAB1 gene. The leaf on the left was from an A11 plant (severe impairment), the center leaf was from an E2 plant (mild impairment), and the leaf on the right from a transformed control.

Many of the plants regenerated from transformed callus cultures possessed a range of characteristic growth defects. Plants from callus lines A1, B1, and F6 were severely impaired (an example of a plant from callus line F6 is shown in FIG. 2, plant A) and developed large necrotic areas on most leaves. Plants from lines A11, A18, and F5 displayed more vigorous growth, but developed necrotic lesions on older leaves (a plant from line A11 is shown in FIG. 2, plant B, and an example of the necrotic lesions that appeared in these plants is illustrated in FIG. 3). Plants regenerated from callus lines A2, A10, C1, D2, E1, and E2 displayed near normal growth (a plant from line E2 is shown in FIG. 2, plant C). However, these plants possessed chlorotic sectors (the center leaf in FIG. 3) on most leaves. Of the 19 callus lines regenerated, nine (lines B2, D1, D3, D4, D5, E3, E5, and F2) yielded plants that displayed no visible growth aberration.

Because of the variability in the appearances between plants derived from different callus lines, the levels of the yPAB in several different lines were evaluated by immunoblot analysis using a monoclonal antibody specific for the yPAB (obtained from Dr. Maurice Swanson, University of Florida). When this was done, yPAB was detected in plants that exhibited growth impairments. In these Western blots, proteins were extracted from primary transformants, separated by SDS-PAGE, transferred to nitrocellulose filters and probed with the aforementioned monoclonal antibodies (data not shown). In addition to the appropriately sized yPAB, a series of lower molecular weight bands was also recognized by this antibody. These smaller polypeptides may represent breakdown products of the yPAB that arise in planta, as our extraction procedure is designed to minimize protease activity after cell breakage.

An excellent correlation was seen between plants that exhibited a novel phenotype (those from lines A2, A10, A18, B1, C1, D2, and F5) and the presence of the yPAB (data not shown). This correlation extended to the quantitative level; plants with the more severe growth impairment (from callus lines A18, B1, D2, and F5) possessed significantly more yPAB than did plants with a mild phenotype (from lines A2, A10, and C1). In addition, none of the plants that lacked a growth phenotype (from lines B2, D1, E1, E3, E5, and F2) contained detectable yPAB.

These data strongly suggest that the expression of the yeast PAB1 gene in tobacco leads to a dramatic growth impairment. This phenomenon is a heritable one; kanamycin-resistant F1 plants derived from several impaired lines displayed the same growth impairment as is seen in the primary transformants (Table 3). Importantly, parents that had severe impairments yielded progeny with similar impairments, and those with mild impairments produced F1 progeny with a mild phenotype as well (data not shown). For two of these lines (A18 and E1), 100% of the kanamycin-resistant progeny were impaired. However, most lines yielded progeny in which the growth impairment segregated. In some of these lines (e.g., A10, A11, and E2), this segregation probably reflected plant-to-plant variability in yPAB levels, as all of the kanamycin resistant progeny possessed detectable yPAB. However, in one line (A2), detectable expression of the yPAB segregated as well. Finally, in the one "normal" line examined (D5), a small percentage of F1 progeny possessed detectable yPAB, indicating that the transgene(s) was functional in this line, but was not sufficiently active to produce yPAB in quantities needed to observe a growth impairment.

The above observations indicate that the expression of the yeast PAB1 gene in tobacco can cause a dramatic impairment of growth of the transgenic plants. This effect could be caused by any of a number of effects, ranging from an effect on the expression of the tobacco PAB gene family to interruptions of specific PAB functions. To evaluate the possibility that the expression of the tobacco PAB gene family was altered in the PAB1 transgenic plants, the levels of the tobacco PAB (tPAB) in PAB1 transgenic lines that displayed severe (A1, A11) or mild (E2) growth impairments were measured by immunoblot analysis. In these Western blots, proteins from the transformed plants were extracted, separated by SDS-PAGE, transferred to nitrocellulose filters and probed with monoclonal antibodies against yPAB or polyclonal antibodies against pea PAB (data not shown). As in the aforementioned study, the levels of the yeast PAB in these lines reflected the degree of growth impairment; in particular, the yPAB levels in the E2 line were about 30 times lower than those in the A1 and A11 lines (data not shown). However, tPAB levels were similar in all of these lines, and were comparable to tPAB levels in "normal" PAB1-transformed lines or in transgenic controls. (The differences in tPAB levels between the different lines are not reproducible; in other experiments, plants from callus lines A1 and A11 are seen to have similar, or somewhat higher, levels of tPAB.) From experiments such as these, it was clear that the tPAB levels were unchanged in PAB1 transgenic lines that displayed severe growth impairments.

A second possible effect of the yPAB in transgenic plants may be to interfere with the tPAB function as a consequence of being present in a large molar excess. However, immunoprecipitation analysis indicated that yPAB levels were less than 20% of tPAB levels (data not shown), indicating that there is no large molar excess of yPAB in the most impaired transgenic lines.

A third possible effect of the yPAB in transgenic plants may be to interfere with the process of poly(A) shortening. To test this possibility, poly(A) lengths in total RNA isolated from severe (A11), mild (E2) and normal (D3) PAB1-transformed plants were determined and compared with controls. For this, RNA from six different plants (two controls, two severely impaired plants, one mildly impaired plant, and one PAB1 plant devoid of visible impairment) was labeled with poly(A) polymerase and [a-$^{32}$P]3'-dATP, the labeled molecules were digested with RNAse A (which will not digest polyadenylate tracts), and the RNAse-resistant fragments were examined on a 6% sequencing gel. This experiment revealed no obvious differences in poly(A) lengths in the different lines; in the six samples shown, poly(A) lengths extended from <40 to >500 nts, and no discernible change in the relative abundance of smaller or larger molecules was observed in the severe or mild lines with respect to the controls or normal PAB1 transformants.

Expression of the Yeast PAB1 Gene does not Affect Callus Growth

As mentioned above, obvious differences between the independent callus lines that were produced were never apparent. This suggested that, although the expression of the yeast PAB1 gene impaired the growth and development of plants, the expression of the same gene had little effect on undifferentiated cells. To explore this, yPAB levels in three lines that had been maintained for more than six months with a transformed control callus culture (of similar age) were compared; these were qualitatively identical in terms of callus morphology, growth vigor, and regeneration potential. One of these callus cultures (A11) was that used to regenerate plant line A11, a line noted above as having a severe growth impairment (FIG. 2) and relatively high yPAB levels (data not shown). As before, proteins were extracted, separated by SDS-PAGE, transferred to nitrocellulose filters, and probed with monoclonal antibodies against yPAB. These studies indicated that there was a broad range of yPAB in the different lines. Importantly, lines with yPAB levels greater than those seen in the A11 line were identified. Additional studies such as this revealed that lines that yielded plants with a mild growth impairment accumulated little yPAB, whereas lines with high levels gave rise to plants with severe impairments (data not shown). This study indicates that the yPAB gene is in fact expressed in undifferentiated plant cells, and that high levels of the yPAB do not significantly impair the growth of such cells.

Plants that Express the Yeast PAB1 Gene are Induced for Systemic Acquired Resistance Plants that express the yeast PAB1 gene at elevated levels (e.g., A1 and A11) display characteristics (progressive chlorosis and necrotic lesions) suggestive of possible constitutive defense or hypersensitive responses, in turn leading to the possibility that such plants might, at a stage in their growth, possess elevated levels of defense-related gene expression and resistance to various pathogens. Accordingly, one such line (A11) was evaluated for resistance to a viral pathogen (tobacco mosaic virus), a bacterial pathogen (*P. syringe* pv *tabaci* WF4), and a fungal pathogen (*Peronospora tabacina* Adam), and for expression of a defense-related gene (the so-called PR1-b gene; 24). For these studies, A11 plants were selected at a stage of growth at which "symptoms" characteristic of the pab1-induced impairment were not yet apparent.

Figure 4A:
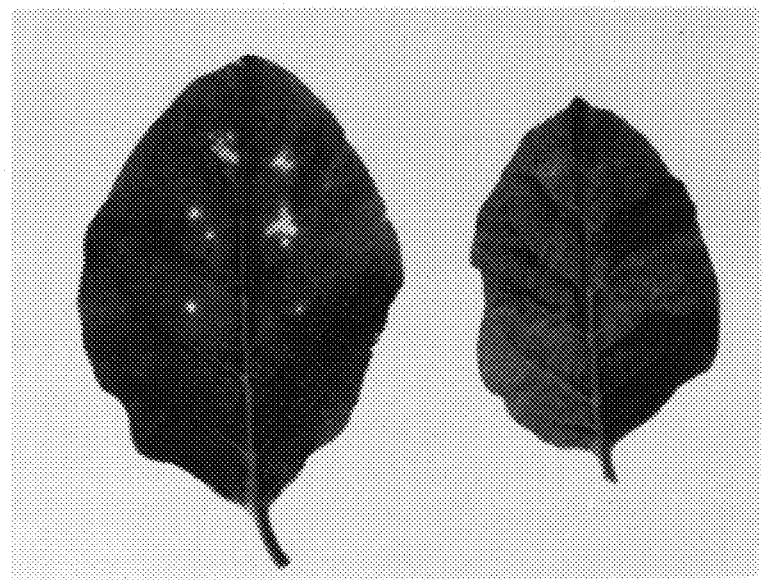
FIGS. 4A and 4B show that the A11 line is resistant to a bacterial and a viral pathogen. Transformed control plants (right) and F1 individuals derived from line A11 (left; see FIG. 2) were inoculated with TMV (A) or *P. syringe* pv *tabaci* WF4 (B). The series of spots seen in the controls represent a series of dilutions of each pathogen. For TMV, the concentrations were, from top to bottom, 0.5, 0.1, 0.02 mg/mL. The spot on the bottom is a water control. In the *P. syringe* pv *tabaci* WF4 test, 200,000 and 20,000 cfu/mL were inoculated on right and the left hand side of the leaf, respectively. The bottom sample was water control.
Figure 4B:
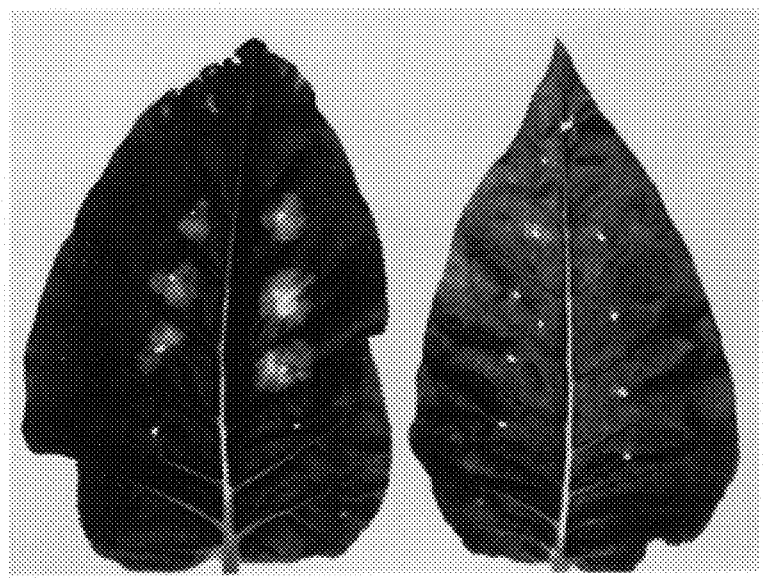
Figure 5:
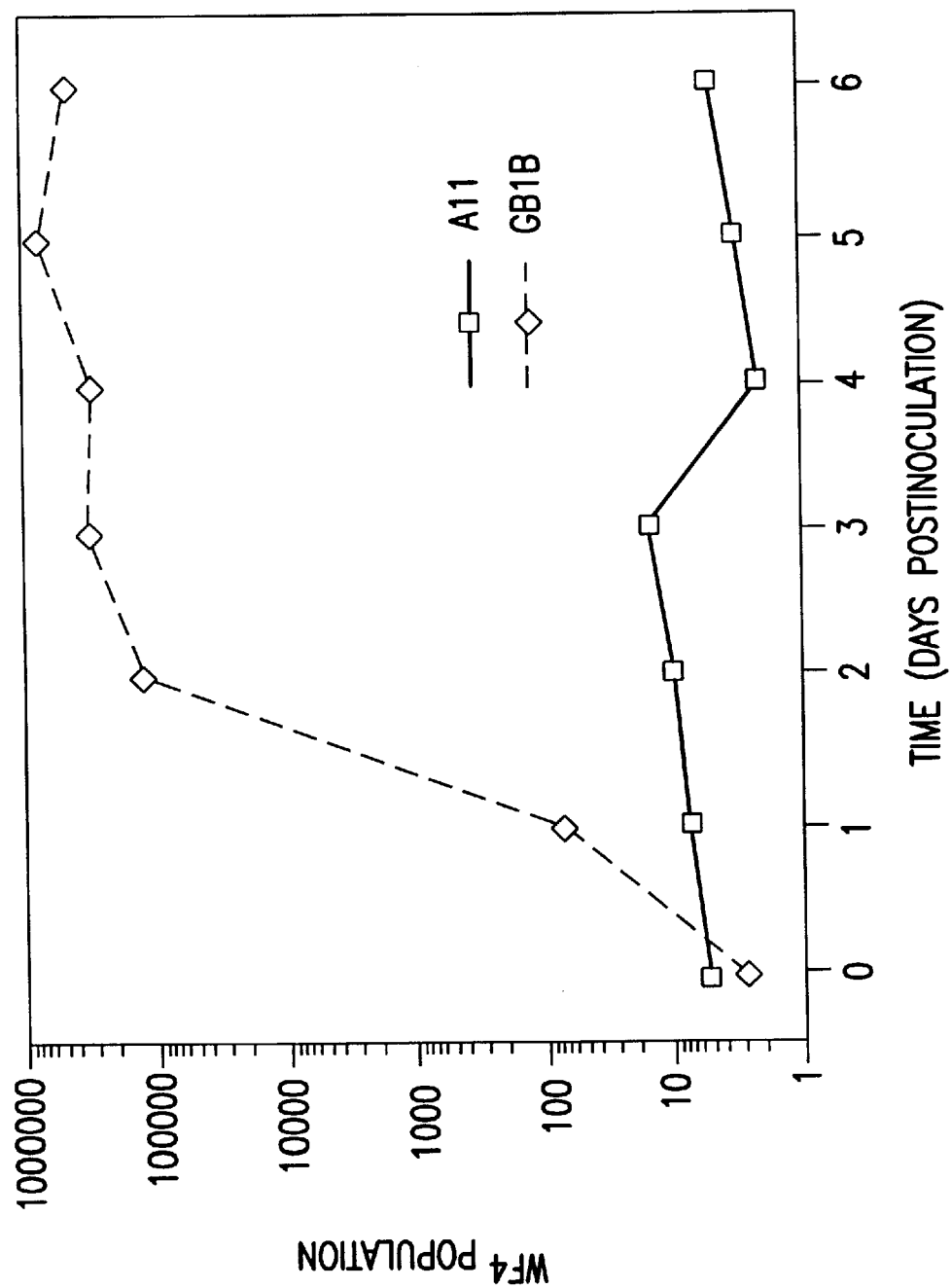
FIG. 5 shows the results of WF4 population counts for line A11 and transformed control GB1B. For bacterial population studies, 20,000 times dilution was used. After infiltration of the WF4 on the tobacco leaf (7 to 8 weeks old plants, 3 plants each line), the infiltrated area was marked for easier sampling. Two leaf discs (diameter=6 mm) were taken from each infiltrated area, washed by 70% ethanol for two minutes, rinsed with water 3 times. Then each leaf disc was ground in 100 mL sterile water, and spun briefly. The supernatant was diluted and spread on LB agar plate for colony counting, after 2 days culture at 30° C. Leaf samples were taken daily from day 0 to day 6.

As shown in FIG. 4, A11 plants were significantly resistant to infection by TMV and WF4. While significant lesions could be seen on the inoculated controls, they were virtually absent from leaves of A11 plants. This visual assay was confirmed, in the case of WF4, by a more quantitative bacterial growth test (FIG. 5). As shown in this study, there was no discernible growth of the bacteria on the A11 leaves over the course of this study. In contrast, the bacterial population increased by approximately 5 orders of magnitude on the control plants. This test indicates that A11 is highly resistant to a bacterial and a viral pathogen, and is consistent with the hypothesis that these plants are constitutively induced for systemic acquired resistance (SAR).

A11 plants were also significantly protected against a fungal pathogen (*P. tabacina*). This is apparent upon visual inspection (not shown) and by determining the growth of the fungus. Transgenic cell lines A11 and E2 are compared with a control and the results are given in Table 4, with the mean of four replications+/−standard error reported per line. This study again supports the hypothesis that these transgenic plants are induced for SAR.

TABLE 4

| Line | Mean no. sporangiospores per cm$^2$ of leaf area (×10$^3$) |
| --- | --- |
| Control | 92.25 +/− 32.6 |
| E2 | 39.00 +/− 14.3 |
| A11 | 15.10 +/− 12.2 |

As another test of this hypothesis, the expression of a pathogenesis-related gene (the PR1-b gene; 24) was examined in the transformed control and in line A11 (without any treatments such as wounding or inoculation with pathogens). In these Northern blot studies, RNA was isolated from a transformed control (GB1B) and the A11 line. The RNA was visualized by hybridization with a probe specific for the tobacco PR1-b gene and by staining with ethidium bromide. No detectable expression was observed in the control line. In contrast, significant PR1-b expression could be seen in the A11 line. This result again supports the hypothesis that SAR is induced in a constitutive manner in the A11 line.

DISCUSSION

These experiments show that expression of the yeast PAB1 gene can impair the growth of tobacco: a majority of independent transgenic plants produced with a yeast PAB1 expression vector displayed a range of characteristic growth abnormalities, and the presence or absence of these abnormalities correlated with the presence of detectable yPAB. Moreover, the growth impairment was heritable and predictable; primary transformants with severe impairments yielded F1 progeny and transformants with mild impairments produced F1 progeny that were correspondingly mildly impaired.

A significant number of the transgenic lines displayed no growth impairment, and they did not accumulate detectable yPAB. However, one such line yielded F1 progeny in which yPAB could be detected (Table 3). This suggests that the range of effects, be they visible phenotype or yPAB expression levels, are a consequence of plant-to-plant variability in the activity of the yPAB transgene. More specifically, this observation indicates that insufficient expression, and not an inadvertent inactivation of the transgene, is responsible for the occurrence of unimpaired plants.

Transgenic plants that express the yeast PAB1 gene contain a number of probable breakdown products that are derived from the full sized yPAB. The relative quantities of these mirror those of the native yPAB in the different lines, and it is possible that the growth impairment we observe is caused by the presence of one or more breakdown products, and not the full sized yPAB. These possibilities cannot be distinguished at this time, but the possible involvement of less than full-length molecules in the impairment may provide a useful tool for dissecting structure-function relationships of PABs in plants.

These studies rule out a number of possible mechanisms for the impairment of growth by the yPAB. The expression of the yeast PAB1 gene does not dramatically suppress expression of the corresponding tobacco genes, as has been seen in other instances of heterologous gene expression in plants (14). However, it has been established that Arabidopsis contains several PAB genes, each expressed in different tissues and at different times during development (6,10). It is likely that tobacco also contains more than one PAB gene. Thus, it is possible that the yeast PAB1 gene may exert its effects through a differential interference of expression of a subset of tobacco PAB genes, and that this effect may not be apparent due to possible differential recognition of tobacco PABs by the antibodies raised against the pea PAB. Such a scenario merits mention as it implies vital roles for different PABs in vegetative growth and development in tobacco.

Immunoprecipitation analyses indicate that the yPAB levels are less than 20% of those of the tPAB (data not shown), indicating that the effects of the yeast PAB1 gene are not due to the presence of a large molar excess of this protein. Poly(A) lengths are similar in impaired PAB1 plants and in unimpaired transgenic or controls, indicating that the yPAB does not act by interfering with poly(A) shortening. Because callus lines that contain high levels of yPAB are as vigorous and long-lived as lines with no detectable yPAB, it is inferred that the yPAB does not affect general translation in plant cells. However, as implied in the preceding section, the effects on poly(A) shortening or translation in specialized cell types cannot be ruled out. Also, the possibility that the yeast PAB accumulates to a great excess over the tobacco PAB in specific cell types cannot be eliminated.

The yPAB protein thus impairs the growth of plants by an as yet unidentified mechanism. However, the observations indicating that lines that express the yeast PAB1 gene possess characteristics of SAR suggest that the growth impairment may be a manifestation of an induction of a hypersensitive response, or of cell death, which is triggered by the yPAB protein. Controlled expression of the yPAB protein, which represses the deleterious effects of this protein while providing an SAR, has been demonstrated. The link between yPAB expression and SAR (and the growth impairment) is not clear, but the possibility that cytoplasmic RNA metabolism may affect defense responses is interesting. In any case, future studies with this system should lead to new and important insight into the functions of PABs and RNA metabolism in plants, and as well into the means by which SAR might be triggered.

The present invention has been described with reference to certain examples, which illustrate various aspects of the invention. It should be appreciated, however, that modifications and improvements to these examples can be practiced within the scope of the appended claims and their equivalents.

TABLE 1

Bacterial Plant Pathogens

| Genus | Disease |
| --- | --- |
| Erwinia | Fireblight, Stewarts' Wilt, Slime Flux, Bacterial Soft Rot |
| Clavibacter | Potato Ring Rot, Alfalfa Bacterial Wilt |
| Corynebacterium | Wheat Bacterial Spike Blight |
| Pseudomonas | Bacterial Blight, Halo Blight of Beans and Oats, Basal Glume Rot and Bacterial Leaf Blight of Wheat |
| Xanthomonas | Bacterial Black Chaff and Bacterial Stripe of Wheat, Bacterial Spot of Peach |

TABLE 2

Viral Plant Pathogens

| Genome type | Virus |
| --- | --- |
| dsDNA | Cauliflower Mosaic Virus, Badnaviruses |
| ssDNA | Geminiviruses |
| dsRNA | Plant Reoviruses, Cryptoviruses |
| RNA Viruses with Negative-Sense or Ambisense Genome | Rhabdoviridae, Tomato Spotted Wilt Virus, Tenuiviruses |
| Positive Sense ssRNA Viruses | Monopartite Genomes: Tobacco Mosaic Virus, Potato Virus X, Potyviridae, Closteroviruses, Turnip Yellow Mosaic Virus, Tomato Bushy Stunt Virus, Luteoviruses, Sequiviridae Bipartite ssRNA: Tobacco Rattle Virus, Cowpea Mosaic Virus, Tobacco Ringspot Virus, Pea Enation Mosaic Virus, Red Clover Necrotic Mosaic Virus Tripartite ssRNA: Brome Mosaic Virus, Cucumber Mosaic Virus, Alfalfa Mosaic Virus, Barley Stripe Mosaic Virus, Beet Necrotic Yellow Vein Virus |

TABLE 3

Inheritance of the selectable marker and yeast PAB1 genes

| Callus line[a] | Pheno-type[b] | % germination[c] | km$^r$:km$^{s(d)}$ | % km$^r$ with symptoms[e] | % km$^r$ with yPAB[f] |
| --- | --- | --- | --- | --- | --- |
| A2 | Mild | 93 | 91:9 | 47 | 67 |
| A10 | Mild | 97 | 96:4 | 32 | 100 |
| A11 | Severe | 94 | 72:28 | 85 | 100 |

TABLE 3-continued

Inheritance of the selectable marker and yeast PAB1 genes

| Callus line[a] | Pheno- type[b] | % germi- nation[c] | km$^r$:km$^{s(d)}$ | % km$^r$ with symptoms[e] | % km$^r$ with yPAB[f] |
|---|---|---|---|---|---|
| A18 | Severe | 97 | 78:22 | 100 | nd |
| C1 | Normal | 96 | 98:2 | 0 | nd |
| D3 | Normal | 85 | 72:28 | 0 | nd |
| D4 | Normal | 89 | 83:17 | 0 | nd |
| D5 | Normal | 97 | 77:23 | 0 | 11 |
| E1 | Mild | 100 | 74:26 | 100 | nd |
| E2 | Mild | 100 | 75:25 | 83 | 100 |
| E5 | Normal | 95 | 78:22 | 0 | nd |
| F2 | Normal | 93 | 87:13 | 0 | nd |
| F5 | Severe | 90 | 83:17 | 51 | nd |

[a]Parental callus line from which the primary transgenic plant used to generate these seed lots.
[b]Degree of growth impairment; normal - no impairment; mild - plants had chlorotic sectors but no obvious necrosis or growth stunting; severe - plants had extensive necrotic areas and were stunted in their growth.
[c]Percent of seeds that germinated on media containing kanamycin.
[d]Percent of kanamycin resistant and sensitive individuals determined by germination on kanamycin-containing media.
[e]The percent of kanamycin-resistant plants that displayed an impairment after six weeks growth (a minimum of 50 plants were scored for each test).
[f]The percentage of kanamycin-resistant plants that possessed detectable yPAB as determined by immunoblot analysis (a minimum of ten plants were scored for each test).

REFERENCES

The pertinent portions of the following references are incorporated herein by reference.
1. Sachs A. et al., *Cell* 58 (1989), 857.
2. Gallie D., *Genes Develop*, 5 (1991), 2108.
3. Bernstein P. et al. *J. Trends Biochem. Sci.* 14 (1989), 373.
4. Bandziulis R., et al. *Genes Develop.* 3 (1989), 431.
5. Haynes S., *The New Biologist* 4 (1992), 421.
6. Hilson P., et al. *Plant Physiol.* 103 (1993), 525.
7. Sachs A. et al. *Mol. Cell. Biol.* 7 (1987), 3268.
8. Sieliwanowicz B., *Biochim. Biophys. Acta* 908 (1987), 54.
9. Yang J. et al. *Plant Physiol.* 98 (1992), 1115.
10. Belostotsky D., et al. *Proc. Nat. Acad. Sci. USA* 90 (1993), 6686.
11. Maiti I., et al., *Proc. Nat. Acad. Sci. USA* 90 (1993), 6110.
12. Horsch R., et al., *Science* 227 (1985), 1229.
13. Mogen B., et al., *Mol. Cell. Biol.* 12 (1992), 5406.
14. Matzke M., et al., *Ann. Rev. Plant Physiol. Plant Mol. Biol.* 44 (1993), 53.
15. Sambrook J., et al., *Molecular Cloning*, 2nd ed. Cold Spring Harbor Laboratory Press, Cold Spring Harbor, N.Y. (1989).
16. Sanger F., et al., *Proc. Nat. Acad. Sci. USA* 74 (1977), 5463.
17. Zambryski P., et al., *EMBO J.* 2 (1983), 2143.
18. Schardli C., et al., *Gene* 61 (1987), 1.
19. Murashige T., et al., *Plant Physiol.* 15 (1962), 473.
20. Towbin H., et al. *Proc. Nat. Acad. Sci. USA* 76, (1979), 4350.
21. Yang J. et al., *Plant Sci.* 99 (1994), 161.
22. Chirgwin J., et al., *Biochemistry* 18 (1979), 5294.
23. Glisin V., et al., *Biochemistry* 13 (1974), 2633.
24. Cornelissen B., et al., *Nucl. Acids Res.* 15 (1987), 6799–6811.
25. Le H., et al. *Eur.J.Biochem.* 243 (1997), 350–357.
26. Berger L., et al. *Biochem. Cell Biol.* 70 (1992), 770–778.
27. Glazebrook et al. Ann. Rev. Genet. 31 (1997) 547–569.

What is claimed is:

1. A method of enhancing resistance of a plant to a bacterial, fungal or viral pathogen comprising:
transforming the plant with a polynucleotide encoding a yeast polyadenylate binding (yPAB) protein; and
maintaining the plant, wherein the yPAB protein is expressed and the plant has enhanced resistance to a bacterial, fungal or viral pathogen as compared to an untransformed plant.

2. The method of claim 1, wherein said transforming is performed on a callus culture or leaf explants, and the plant is regenerated from said callus culture or leaf explants.

3. The method of claim 1, wherein said transforming is performed with an Agrobacterium vector.

4. The method of claim 1, wherein the polynucleotide comprises a CaMV promoter, which regulates expression of the yPAB protein.

5. The method of claim 4, wherein the CaMV promoter is the 35S$^2$ promoter.

6. The method of claim 1, wherein the yPAB protein is yPAB1.

7. The method of claim 1, wherein the plant is selected from the group consisting of corn, rice, wheat, maize, alfalfa, oats, barley, rye, sorghum, clover, tobacco, tomato, pea, potato, cauliflower, beans, cucumber, beet, turnip, spinach, kale, cabbage, squash, melon, cotton, apple, peach, and plum.

8. The method of claim 1, wherein the bacterial pathogen is from a genus selected from the group consisting of Erwinia, Clavibacter, Corynebacterium, Pseudomonas, and Xanthomonas.

9. The method of claim 1, wherein the fingal pathogen is selected from the group consisting of Ascomycetes, Basidiomycetes, Zygomycetes, Oomycetes, Deuteromycetes, Peronosporomycetes, Chytridiomycota, Zygomycota, Plectomycetes, Loculoascomycetes, Discomycetes, Pyrenomycetes, Heterobasidiomycetes, Homobasidiomycetes, Teliomycetes, Ustomycetes, Septomycetes, Saprolegniomycetidae, and Plasmodiophorida.

10. The method of claim 1, wherein the viral pathogen is a cytoplasmic plant virus.

11. The method of claim 1, wherein the viral pathogen is selected from the group consisting of cauliflower mosaic virus, badnaviruses, geminiviruses, reoviruses, cryptoviruses, rhabdoviridae, tomato spotted wilt virus, tenuiviruses, tobacco mosaic virus, potato virus X, potyviridae, closteroviruses, turnip yellow mosaic virus, tomato bushy stunt virus, luteoviruses, sequiviridae, tobacco rattle virus, cowpea mosaic virus, tobacco ringspot virus, pea enation mosaic virus, red clover necrotic mosaic virus, brome mosaic virus, cucumber mosaic virus, alfalfa mosaic virus, barley stripe mosaic virus, and beet necrotic yellow vein virus.

12. The method of claim 1, wherein said resistance is inheritable.

13. The method of claim 1, wherein a pathogen resistance (PR) gene is activated concurrent with the resistance to a bacterial, fungal or viral pathogen.

14. A plant transformed with a polynucleotide comprising a nucleotide sequence encoding a yPAB protein.

15. The plant of claim 14, wherein the yPAB protein is yPAB1.

16. The plant of claim 14, wherein the polynucleotide comprises a CaMV promoter operably linked to the nucleotide sequence encoding a yPAB protein.

17. The plant of claim 16, wherein the CaMV promoter is the 35S$^2$ promoter.

18. The plant of claim 14, which has enhanced resistance to a bacterial, fungal or viral pathogen relative to a plant not transformed with said polynucleotide.

19. The plant of claim 14, which is selected from the group consisting of corn, rice, wheat, maize, alfalfa, oats, barley, rye, sorghum, clover, tobacco, tomato, pea, potato, cauliflower, beans, cucumber, beet, turnip, spinach, kale, cabbage, squash, melon, cotton, apple, peach, and plum.

20. A callus culture or leaf explant transformed with a polynucleotide that encodes a yeast PAB protein.

* * * * *